Figure 1:
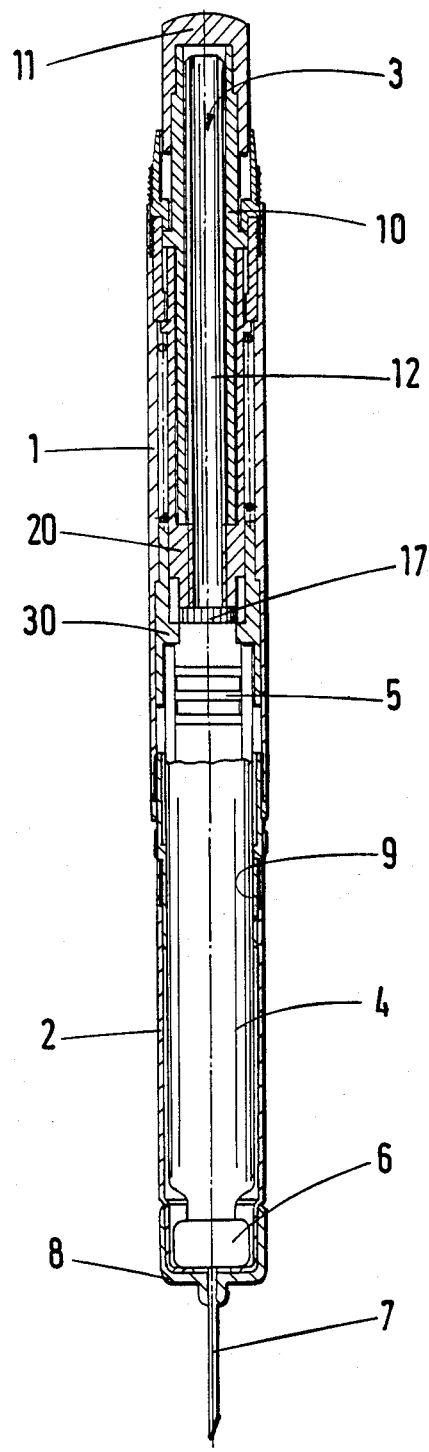

United States Patent [19]

Michel

[11] Patent Number: 4,883,472

[45] Date of Patent: Nov. 28, 1989

[54] INJECTION DEVICE

[75] Inventor: Peter Michel, Burgdorf, Switzerland

[73] Assignee: Disetronic Ag., Burgdorf, Switzerland

[21] Appl. No.: 80,561

[22] Filed: Jul. 31, 1987

[30] Foreign Application Priority Data

Nov. 8, 1985 [CH] Switzerland .................... 04 805/85

[51] Int. Cl.⁴ .............................................. A61M 5/24
[52] U.S. Cl. .................................... 604/208; 604/187; 604/232; 222/386
[58] Field of Search ................ 604/187, 206, 207–209, 604/211, 218, 220, 224, 228, 229, 232; 222/386, 390, 391

[56] References Cited

U.S. PATENT DOCUMENTS

| | | | |
|---|---|---|---|
| 2,221,739 | 11/1940 | Reiter | 604/210 |
| 2,632,445 | 3/1953 | Kas, Sr. | 604/209 |
| 3,110,310 | 11/1963 | Cislak | 604/209 |
| 3,481,510 | 12/1969 | Allen, Jr. | |
| 3,517,668 | 6/1970 | Brickson | 604/209 |
| 3,583,399 | 6/1971 | Ritsky | 604/232 |
| 3,977,574 | 8/1976 | Thomas | 604/209 |
| 4,099,548 | 7/1978 | Sturm et al. | 604/209 |
| 4,333,458 | 6/1982 | Margulies et al. | 604/220 |
| 4,413,760 | 11/1983 | Paton | 222/391 |
| 4,425,121 | 1/1984 | Young et al. | 604/209 |
| 4,444,560 | 4/1984 | Jacklich | 222/391 |
| 4,498,904 | 2/1985 | Turner et al. | 604/211 |
| 4,581,022 | 4/1986 | Leonard et al. | 222/391 |
| 4,592,745 | 6/1986 | Rex et al. | 604/232 |
| 4,659,327 | 4/1987 | Bennett et al. | 604/209 |
| 4,664,128 | 5/1987 | Lee | 604/187 |
| 4,710,172 | 12/1987 | Jacklich et al. | 604/209 |
| 4,710,178 | 12/1987 | Leonard et al. | 604/232 |
| 4,820,287 | 4/1989 | Leonard | 604/224 |

FOREIGN PATENT DOCUMENTS 0058536 8/1982 European Pat. Off. .
1070784 5/1957 Fed. Rep. of Germany .

Primary Examiner—Stephen C. Pellegrino
Assistant Examiner—Ralph Lewis
Attorney, Agent, or Firm—Brady, O'Boyle & Gates

[57] ABSTRACT

An exchangeable prefilled syringe (4) is arranged in the front part (2) of the device. In the rear part (1), a gear mechanism (3) is arranged, the drive member of which is a driving sleeve (10) provided with a manipulating head (11), and the driven member of which is a threaded rod (12) mounted non-rotationally but longitudinally displaceably in the driving sleeve. The threaded rod (12) is seated in the female thread (22) of a gear element (20) which can be advanced, by exerting pressure on the manipulating head (11) in the axial longitudinal direction from a rest position into an end position against the force of a spring (26).

In the rest position of the gear element (20), the threaded rod (12), located at a distance from the plunger (5) of the prefilled syringe (4), is threaded, by rotating the manipulating head (11), through the female thread (22) of the gear element (20) in correspondence with a plunger path required for the amount of liquid to be respectively injected, without the threaded rod (12) abutting against the plunger (5) during this step. Thereafter, the needle (7) is inserted, and the gear element (20) is advanced, by exerting pressure on the manipulating head (11), from the rest position into the end position. During the advancing stroke (h), the threaded rod (12) abuts against the plunger (5) and advances the latter in correspondence with the preselected plunger path.

The device makes it possible to preselect an arbitrary amount of liquid by a corresponding rotation of the manipulating head (11) and to inject this amount of liquid, after insertion of the needle, by means of a single pressure exertion on the head (11).

16 Claims, 6 Drawing Sheets

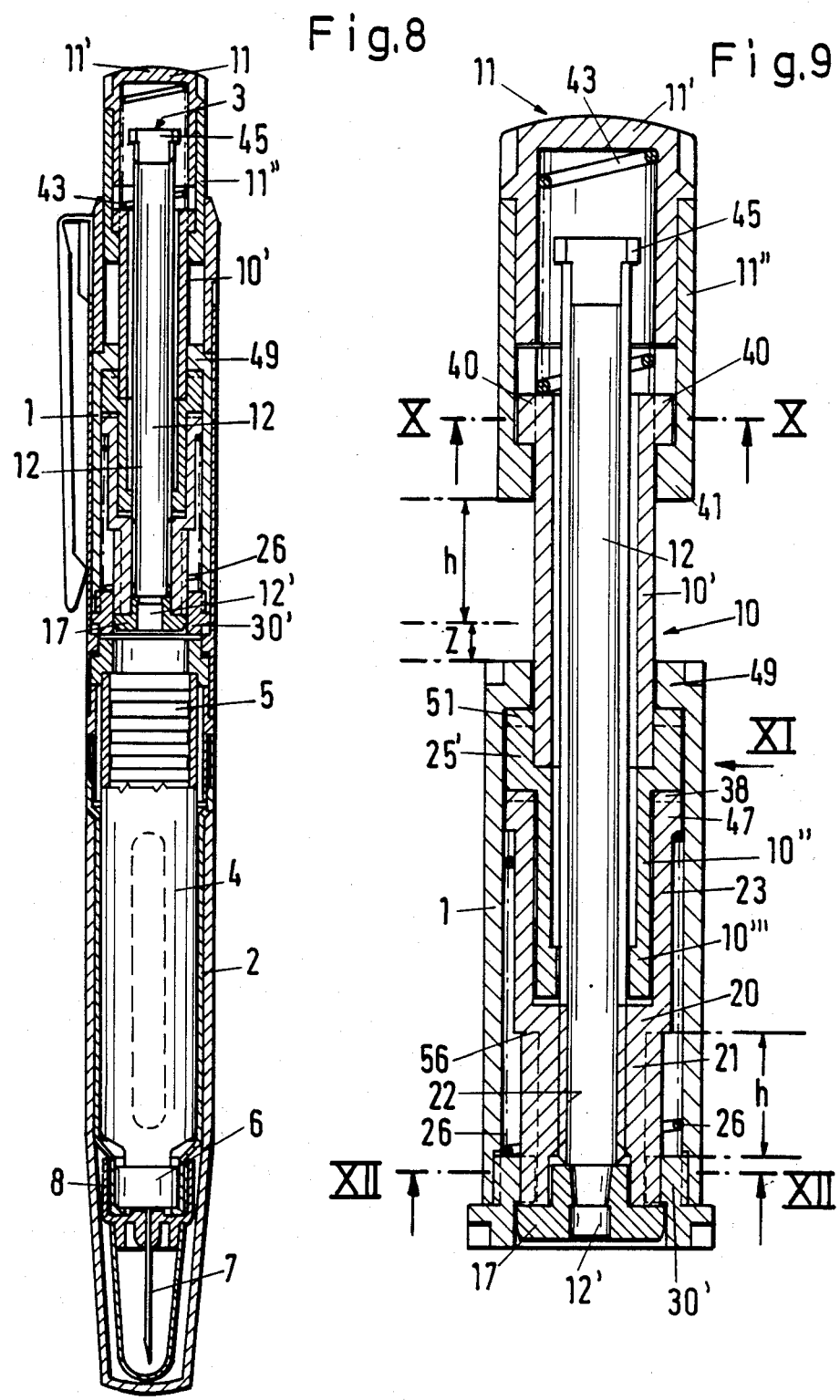

INJECTION DEVICE

The invention relates to an injection device or a dispenser device for dispensing selectable amounts of liquid from a prefilled liquid container that is equipped with a plunger, by advancing the plunger to dispense the liquid.

A device of this type has been known from EP-A No. 0 058 536. In this device, the plunger of the prefilled syringe is advanced by rotating the drive member of a gear mechanism, the driven member of which is constituted by a threaded sleeve in contact with the plunger. The rotating motion of the drive member is limited by a stop, and a coupling means takes care that the drive member can be turned backwards away from the stop without engagement with the gear mechanism. The drive member is in each case turned back prior to injection by an angle of rotation corresponding to the desired amount of liquid and then, during injection, turned forwards until it abuts the stop.

The conventional device cannot be used to perform an injection into one's own arm, because during injection the device must be held with one hand, and the drive member must be turned with the other hand. Furthermore, when the turning step is limited by a stop, there is the danger that the device and thus also the needle are tilted. An especially grave drawback resides in that only a small amount of liquid can be injected with one turning motion, and, for injection of a relatively large amount of liquid, the drive member—with the needle having been inserted—would have to be turned back and forth repeatedly.

The invention is based on the object of providing an injection device wherein an amount of liquid respectively to be injected and being of arbitrary size can be exactly preset and/or preselected, and can be injected by means of a single pressure-exerting movement in the longitudinal direction of the housing.

This object has been attained in accordance with this invention by providing a driven member spaced a distance from the plunger of an ampoule or container of a liquid to be dispensed or injected. The driven member is threadably connected to a supporting element and can be axially advanced from the supporting element and toward the plunger by any desired distance by rotating a coaxially arranged displacing sleeve or drive sleeve that rotates the driven member and also is in contact with the supporting element. The displacing sleeve when moved axially displaces the supporting element together with the connected driven member axially forward and back by a constant axial stroke h between a rearward rest position to a forward end position and back again to the rearward rest position. With this construction, the driven member located at a distance from the plunger in the rearward rest position of the supporting element, can be moved by means of the displacing sleeve, in the advancing direction by the selected distance without abutting against the plunger, and then abuts against the plunger during the axial displacement of the supporting element at the moment the supporting element has been displaced by the difference between the length of the constant stroke h and the selected set axial distance, and then pushes the plunger forward by the selected set distance dispensing the corresponding selected amount of liquid. When the displacing sleeve is released, the driven member moves away from the plunger by the distance of the constant stroke h leaving the plunger in the forward pushed position in the ampoule when the supporting element is displaced back to its rest position.

Figure 2:
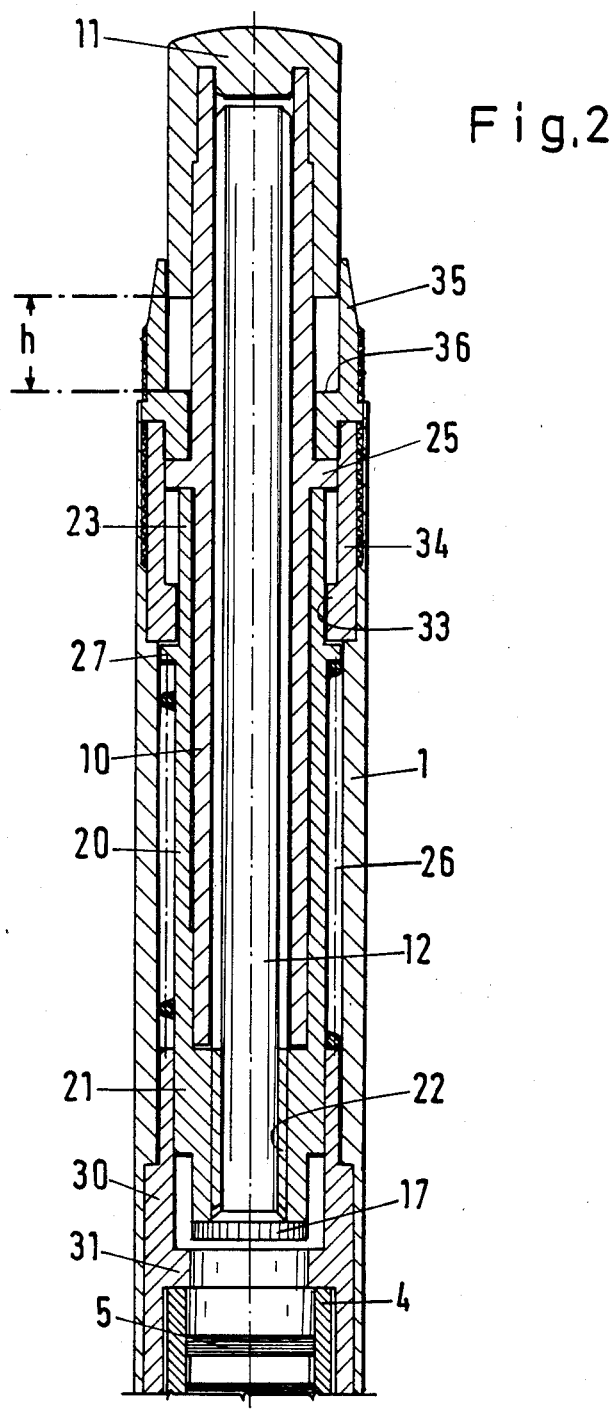
Figure 3:
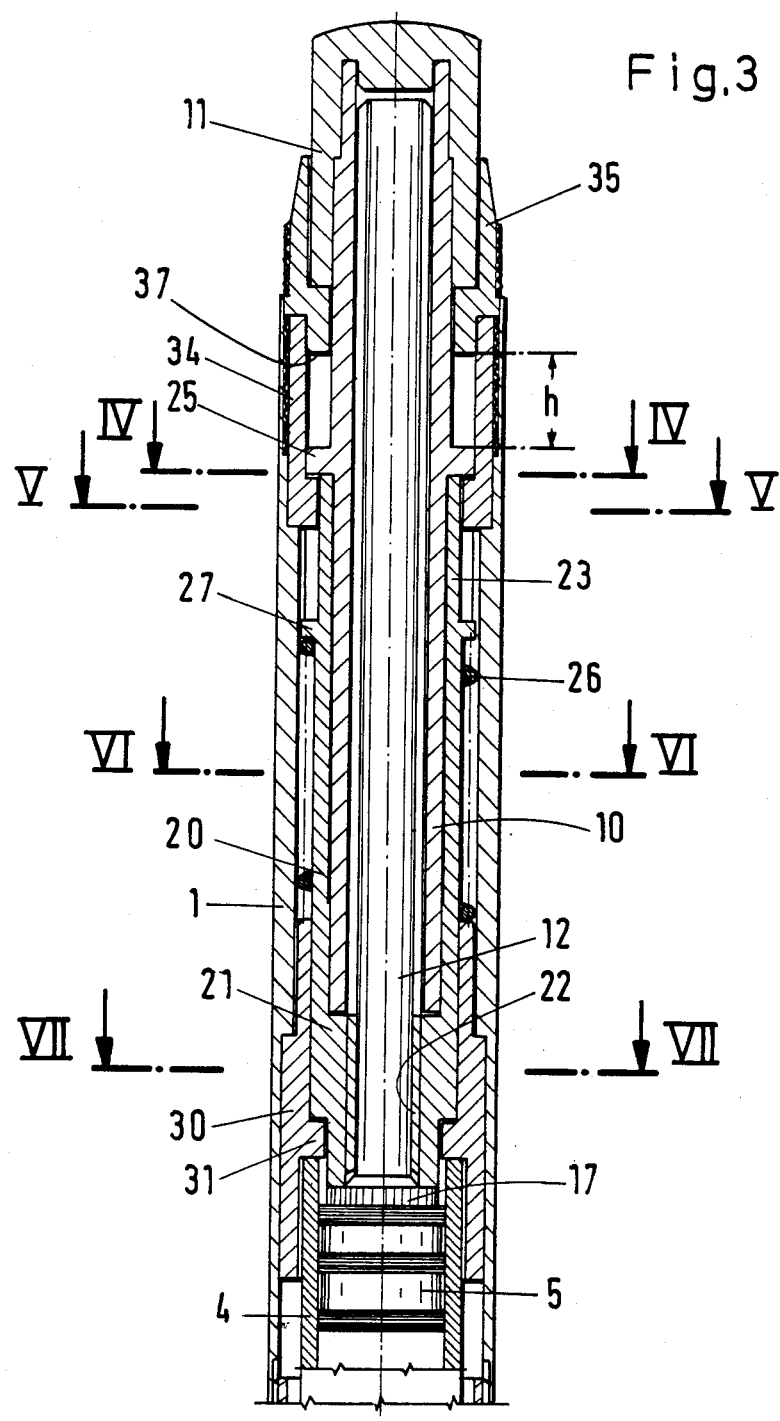
Figure 4:
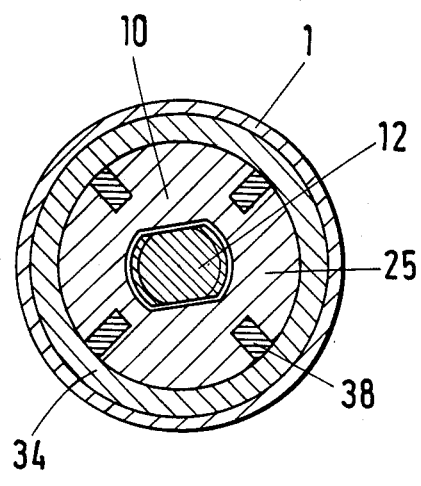
Figure 5:
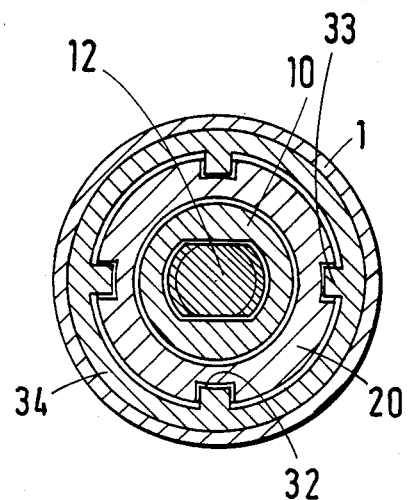
Figure 6:
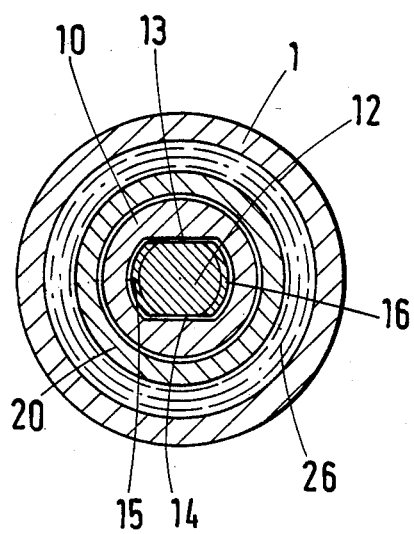
Figure 7:
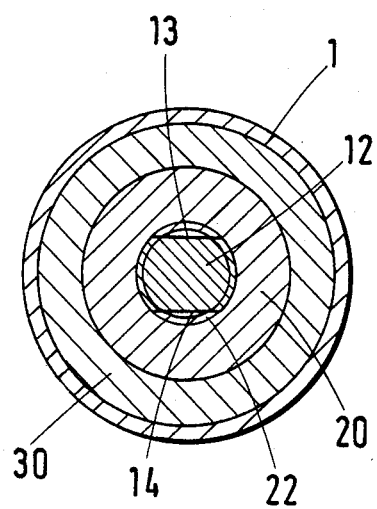
Figure 10:
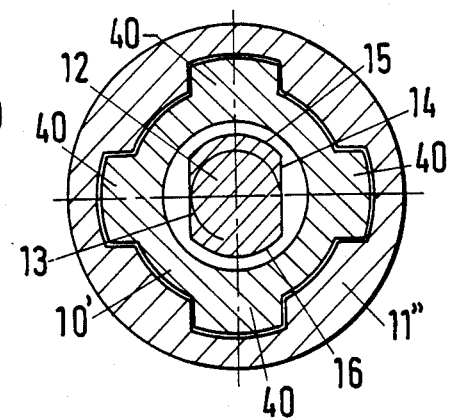
Figure 11:
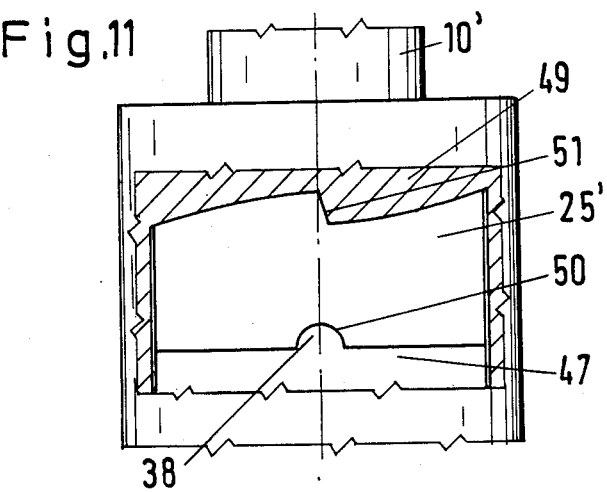
Figure 12:
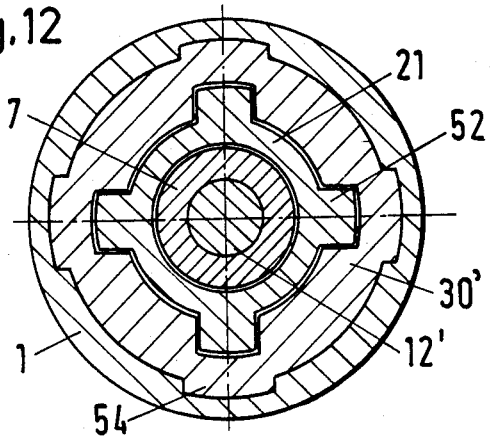

Embodiments of the invention will be described in greater detail below with reference to the drawings wherein:

FIG. 1 is an axial longitudinal section through an injection device wherein the gear element is in the rest position, FIG. 2 is an axial longitudinal section through the rear portion of the device of FIG. 1, on an enlarged scale, FIG. 3 is an axial longitudinal section corresponding to FIG. 2 through the rear portion of the device wherein the gear element is in the end position, FIG. 4 is a cross section along line IV—IV in FIG. 3, FIG. 5 is a cross section along line V—V in FIG. 3, FIG. 6 is a cross section along line VI—VI in FIG. 3, FIG. 7 is a cross section along line VII—VII in FIG. 3, FIG. 8 is an axial longitudinal section through a preferred version of the injection device wherein the gear element is in the rest position, FIG. 9 is an axial longitudinal section through the rear portion of the device (without the housing) of FIG. 8, on an enlarged scale, FIG. 10 is a cross section along line X—X in FIG. 9, on an enlarged scale, FIG. 11 is a lateral view of part of the device in the viewing direction XI in FIG. 9, on an enlarged scale, and FIG. 12 is a cross section along line XII—XII in FIG. 9, on an enlarged scale.

The injection device shown in FIGS. 1-7 comprises two tubular housing sections 1, 2. In the rearward housing section 1 (at the top in the drawing), a gear mechanism 3 is arranged; in the forward housing section 2 (at the bottom in the drawing), a prefilled syringe 4, or injection ampule, also called "carpule" is located. This is an injection ampule destined, in contrast to customary ampules, for use as a conventional prefilled syringe, having at one end a tightly closing plunger 5 (without plunger rod), adapted to receive a plunger rod, and at the other end an outlet section 6 closed by a diaphragm (not shown). The housing section 2 exhibits at the front a cap member 8 supporting the outlet section 6 and provided with a passage for the needle 7. The two housing parts 1 and 2 are joined by a threaded sleeve 9, the rear housing part 1 being glued to the threaded sleeve and the front housing part 2 being detachable by threading from the threaded sleeve in order to exchange the prefilled syringe 4.

The drive member of the gear 3 consists of a driving sleeve 10 on which is seated a manipulating head 11 serving for turning of the driving sleeve 10 and for urging the latter in the forward direction (downwards). The driven member of the gear 3 consists of a threaded rod 12 inserted nonrotationally but longitudinally displaceably in the driving sleeve 10. For the nonrotational mounting, the threaded rod 12 is flattened on opposite faces 13 and 14, and the threadless bore of the driving sleeve 10 is adapted correspondingly.

The threaded rod 12 thus has two planar, parallel, smooth (threadless) longitudinal surfaces 13, 14 along which the rod is entrained by the corresponding, planar inner wall surfaces of the driving sleeve 10, and two cylindrical shell segments 15, 16 provided with the thread, these segments being located at a spacing from the two smooth (threadless) cylindrical inner wall surfaces of the sleeve 10. A disk 17 is arranged on the front end of the threaded rod 12; this disk serves for advancing the plunger 5 described further below.

The gear element or supporting element at which the threaded rod 12 is movably mounted is denoted by 20. The forward portion 21 of the gear element 20 has a female thread 22 through which the threaded rod 12 is threaded. The rear portion 23 of the gear element has a threadless bore wherein the driving sleeve 10 is rotatably mounted. The driving sleeve 10 has a circular-ring-shaped (flange-like) collar 25 resting on the rear end of the gear element portion 23.

By exerting pressure on the head 11 of the driving sleeve 10, the gear element 20 can be shifted from the rest position shown in FIGS. 1 and 2 against the bias of a compression spring 26 into the end position illustrated in FIGS. 3–7. Once the head 11 is released, the gear element 20 is pushed back into the rest position by the compression spring 26.

The compression spring 26 is a coil spring extending around the central portion of the gear element 20. This coil spring engages a collar 27 formed at the element 20 and is supported on a tubular supporting member 30 constituting a guide means for the front part of the gear element 20 and comprising a supporting ring 31 projecting radially inwardly; this supporting ring rests on the rearward rim of the ampoule 4. The cylindrical shell of the gear element 20 extending toward the front from collar 27 is adapted with a clearance to the tubular supporting member 30 and tapers at the front end to adapt to the supporting ring 31. The cylindrical shell of the gear element 20, extending from the collar 27 in the rearward direction, is adapted with a clearance to the guide means 34 and exhibits four longitudinal grooves 32 arranged at equal spacings from one another. Four longitudinal ribs 33 engage into the grooves 32, these ribs being formed at the front part of a guide means 34 firmly anchored in the housing section 1, so that the gear element 20 is supported nonrotationally but with longitudinal displacement ability at the forward end of the guide means 34. The rear part of the guide means 34 has a bore adapted to the circular-ring-shaped collar 25 of the driving sleeve 10, and a guide head 35 is seated on the rear end of this rear part of the guide means. The front part of the guide head 35 is adapted to the driving sleeve 10, the rear part to the operating head 11. The annular shoulder or stepped surface 36 (FIG. 2) at the transition between the bore of the guide head 35 adapted to the sleeve 10 and the bore adapted to the head 11 constitutes an abutment for the manipulating head 11. This abutment 36 limits the advancing motion of the operating head 11 and thus also the shifting of the gear element 20. The end position of the gear element 20 shown in FIGS. 3–7 thus has been reached once the manipulating head 11 abuts against the stop 36. (Of course, the end position could also be defined by abutment of the collar 25 against the lower portion of the guide means 34, or by abutment of the gear element 20 against the supporting ring 31.)

In the rest position of the gear element 20 illustrated in FIGS. 1 and 2, the collar 25 of the driving sleeve 10 is urged against the forward end 37 (FIG. 3) of the guide head 35 by the gear element 20 which is under the bias of the spring 26. The collar 27 of the gear element 20 exhibits, in the rest position, a small spacing from the front end of the guide means 34.

In order to be able to accurately preselect the amount of fluid to be respectively injected, a stop mechanism is provided which locks in position repeatedly during each complete revolution of the operating head 11, in the present embodiment four times, so that after each revolution by 90 degrees, a tangible locking resistance must be overcome. The stop mechanism is constituted by four diametrically extending cams 38 arranged at angular spacings of 90 degrees on the rearward, annular end face of the gear element portion 23, and by corresponding, channel-like indentations in the annular surface of the collar 25 of the driving sleeve 10, this annular surface facing the gear element 20. The cams 38 and the indentations have a round cross section so that the stop positions can be overcome effortlessly, but yet against tangible locking resistance. The spring 26 urging the end face of the gear element 20, provided with the cams 38, against the surface of the collar 25 equipped with the indentations forms the detent spring of the stop mechanism.

The mode of operation of the above-described injection device will now be described, starting with the following initial position: The gear mechanism 3 is in the position shown in FIGS. 1 and 2. In this case, the driving sleeve 10 and the gear element 20 are held in the rest position by means of the spring 26, the collar 25 being in contact with the stop 37. The threaded rod 12 has been threaded completely backwards so that the disk 17 is in contact with the front end of the gear element 20. A full prefilled syringe 4 is inserted in the device. Its plunger 5 is seated in the rear end of the ampoule, namely somewhat more toward the rear than illustrated in FIGS. 1 and 2.

First of all, care must be taken to fill the needle 7 with liquid. For this purpose, the head 11 is pressed toward the front (downwards) until it abuts against the stop 36. During this feed stroke h, the collar 25 urges the gear element 20, with the threaded rod 12 seated in its female thread 22, in the forward direction against the force of the spring 26, the disk 17 abutting against the plunger 5 and advancing the latter so that a small amount of liquid will exit from the needle 7. At the end of feed stroke h, all parts have assumed the positions shown in FIGS. 3–7: The driving sleeve 10 and the gear element 20 are in the end position defined by the abutment of the head 11 against the stop 36; the disk 17 contacts the plunger 5.

Upon releasing the head 11 at this point, the spring 26 presses the gear element 20 and thus also the threaded rod 12 seated in its thread 22, with the disk 17 as well as the driving sleeve 10, toward the rear until the collar 25 abuts against the stop 37. Thus, all parts have assumed the position shown in FIGS. 1 and 2: The gear element 20 and the driving sleeve 10 are in their rest position supported by the spring 26, and the disk 17 has a spacing h from the plunger 5 corresponding exactly to the stroke h of the gear element 20 between the rest and end positions. The device is now ready for operation.

In order to inject a specific amount of liquid, the head 11, with the gear element 20 being in the rest position according to FIGS. 1 and 2, is first of all turned (before inserting the needle 7). During this process, after each revolution by 90 degrees, the locking resistance of the stop mechanism 38 must be overcome. Each revolution by 90 degrees corresponds to a liquid unit, so that the amount of liquid to be injected is measured in accordance with the number of stop positions to be overcome. During rotation of the driving sleeve 10, the threaded rod 12 entrained by the latter is threaded forwardly through the female thread 22 of the gear element 20, the spacing between the disk 17 and the plunger 5 being diminished without the disk coming into contact with the plunger. (The stroke h of the gear element 20 is dimensioned to be larger than the plunger path required for the injection of a maximally permissible quantity of liquid.) After the head 11 has been turned in correspondence with the desired amount of liquid, the needle 7 is inserted, and the head 11 is pressed up to the stop 36, the gear element 20 being advanced from the rest position shown in FIGS. 1 and 2 into the end position illustrated in FIGS. 3-7. During this advance stroke h, the disk 17 abuts against the plunger 5 and advances the latter to exactly the extent to which the threaded rod 12 had been rotated forwards by the preceding turning of the head 11 with respect to the gear element 20. After releasing the head 11, the spring 26 urges the gear element 20 again into the rest position, the disk 17 receding from the plunger 5 by the stroke h. For the subsequent injection, tee head 11, as described above, is again turned in correspondence with the desired amount of liquid and then pressed downwards. In order to inject exactly the set quantity of liquid, the feed stroke would have to be performed fundamentally either always with the stop mechanism being engaged, or always with the stop mechanism being unlocked. The height of the cam 38 of the stop mechanism, however, is made so low (for example only two tenths of a millimeter in height) that the difference between the feed stroke in case of the engaged position and in case of the unlocked position is negligible for the injected quantity of liquid, i.e. this difference is smaller than the longitudinal path of the threaded rod in case of a revolution by 90 degrees.

Once the ampoule is empty, the housing section 2 is disengaged by threading from the threaded sleeve 9, and the empty ampoule 4 is removed. During this step, the supporting member 30 carried with its ring 31 by the rear end of the ampoule 4 drops downwardly onto the threaded sleeve 9. The spring 26 is relieved, and the gear element 20 is no longer pressed against the collar 25. The head 11 can now be turned back without having to overcome the locking resistances. This is of importance because, prior to insertion of the filled ampoule, the threaded rod 12 must be threaded backwards completely through the female thread 22, requiring very many revolutions. After the threaded rod 12 has been turned backwards, the housing section 2, with a new, full ampoule 4 inserted therein, is again threadedly connected with the threaded sleeve 9, the ampoule again shifting the supporting member 30 into the position shown in the drawing. Thus, the starting position described in the foregoing has again been attained.

For protection of the needle 7 and of the manipulating head 11, respectively one cap (not shown) can be placed at the front and at the rear onto the housing sections 1 and 2.

In the embodiment illustrated in the drawing, the forward end of the driving sleeve 10 has a spacing from the front part 21 of the gear element 20 exhibiting the female thread 22. The driving sleeve 10, however, can also be in contact with the front part 21, and the stop mechanism can be constituted by projections and indentations on these mutually contacting surfaces. In this case, the collar 25 has a distance from the rear end of the gear element 20. Furthermore, the stop mechanism could also be formed by projections and indentations on the surfaces of the collar 25 of the driving sleeve 10 and of the stop 37, brought into mutual contact under the force of the spring 26. The spring 26 could also be supported directly on the rearward rim of the ampoule 4, instead of being supported on the supporting member 30.

FIGS. 8-12 illustrate a preferred variation of the injection device of FIGS. 1-7. The parts of this version corresponding to the parts of the injection device mentioned in connection with FIGS. 1-7 bear identical reference numerals in FIGS. 8-12. This version differs as follows from the embodiment of FIGS. 1-7:

The driving sleeve 10 constituting the drive member of the gear 3 consists of two parts 10', 10'' fixedly joined together. The rear (upper) end of the part 10'' has a collar 25' projecting radially outwardly, the front (lower) end of part 10' being seated therein; the front end has an extension 10''' projecting radially inwardly and surrounding the threaded rod 12. The manipulating head 11, consisting of two parts 11', 11'' firmly joined to each other is mounted, rather than being firmly seated on the driving sleeve part 10', so that it is merely fixed with respect to rotation, but is displaceable longitudinally. For this purpose, the sleeve part 10' has at its upper end four guide ribs 40 extending in the longitudinal direction of the housing, these ribs engaging into corresponding grooves provided on the inner wall of the head part 11'' and extending in the longitudinal direction of the housing (FIG. 10). The front end of the head part 11'' has an extension 41 which projects annularly inwardly and encompasses the driving sleeve part 10'. A compression spring 43 is clamped in the cavity of the head 11 between the cover part of the head section 11' and the upper end rim of the sleeve part 10'. In the rest position shown in FIGS. 8 and 9, the head 11 is held by means of its extension 41 at the ribs 40 against the force of the spring 43.

The threaded rod 12, constituting the driven member of the gear 3, is flattened over its entire length on opposite sides 13 and 14, but is mounted nonrotationally only in the extension 10''' of the driving sleeve 10. Thus, only this extension 10''' of the driving sleeve has an inner wall, adapted to the threaded rod 12, with two planar and two cylindrical (smooth) inner wall surfaces (corresponding to FIGS. 4-6). The remaining portion of the driving sleeve 10 has a cylindrical bore, the diameter of which is larger by one tolerance than the diameter of a flange 45 formed at the upper end of the threaded rod 12. When the threaded rod 12 is threaded through the female thread 22 of the front part 21 of the gear element 20, the flange 45 travels forwards (downwardly) through the driving sleeve 10 until it abuts against the stop 10'''' of the driving sleeve.

The front end of the threaded rod 12 carries a peg 12' on which is seated the disk 17 serving for advancing the plunger 5.

The compression spring 26 engages at a collar 47 formed at the rear end of the gear element section 23 and is supported on a supporting member 30' fixedly held in the housing 1, 2. By means of the spring 26, the collar 47 is urged against the collar 25' formed at the driving sleeve, and this last-mentioned collar, in turn, is pressed against a shoulder 49 formed at the rear end of the housing part 1 and surrounding the driving sleeve portion 10'. The mutually contacting faces of collars 47 and 25' exhibit respectively four cams 38, extending radially at angular spacings of 90°, and channel-like indentations 50 adapted to these cams, constituting a stop mechanism under the action of spring 26. The stop mechanism formed by the cams 38 and indentations 50 corresponds to that described in connection with FIGS. 1–7. The mutually contacting surfaces of the collar 25' and of the shoulder 49 each exhibit a mutually adapted sawtooth profile 51 (FIG. 11) forming a locking mechanism under the action of spring 26. The sawtooth profiles 51 on the mutually adjoining faces of collar 25' and shoulder 49 have respectively four teeth arranged at angular distances of 90°, the four tooth flanks at the collar 25' lying, in the longitudinal direction of the housing, exactly above the indentations 50 of the collar 25', and the four tooth flanks on the shoulder 49 lying, in the longitudinal direction of the housing, exactly above the cams 38 of the gear element portion 23. The gear element 20 can be displaced, secured against rotation, in the supporting member 30' by means of guide ribs 52 provided at its front part 21; the supporting member 30' is fixedly anchored in the housing 1, 2 and secured against rotation in the housing by means of ribs 54 (FIG. 12). The gear element 20 can be shifted against the force of spring 26 from the rest position illustrated in FIGS. 8 and 9 by the stroke h in the forward (downward) direction, i.e. by such a distance until the shoulder 56 of the gear element 20, formed at the transition between the forward and rearward portions 21 and 23 of the gear element 20, abuts against the supporting member 30'.

The elasticity constant of the spring 43 is—as will be explained below—higher than that of spring 26, i.e. the spring 43 is harder than spring 26 so that upon exerting pressure on the head 11, the spring 26 is first compressed until the shoulder 56 abuts against the supporting member 30', and only when the head is further depressed will the spring 43 be compressed.

The mode of operation of the modified embodiment of the injection device will now be described, starting with the initial position illustrated in FIGS. 8–12 wherein the threaded rod 12 has been threaded completely rearwards so that the disk 17 contacts the front end of the gear element portion 21, and the plunger 5 is located at the very rear within the filled injection ampoule 4. Prior to the first injection, after removing the protective caps securing the needle 7, the head 11 is pressed forwards (downwards) to fill the needle 7 with liquid. Since the spring 43 is stiffer than the spring 26, the head 11 initially remains in its position with respect to the driving sleeve 10 as illustrated in FIGS. 8/9. The pressure force exerted on the head 11 is transmitted by the spring 43 to the driving sleeve 10 which latter engages at the collar 47 of the gear element 20 and presses the latter, together with the threaded rod 12 seated in its female thread 22, forwardly (downwardly) against the bias of the spring 26 until the shoulder 56 abuts at the supporting member 30'. The head 11, the driving sleeve 10 and the threaded rod 12 thus are moved forwardly by the stroke h with respect to the housing 1/2, during which step the disk 17 mounted on the peg 12' of the threaded rod 12 comes into contact with the plunger 5 during the stroke h and then drives this plunger somewhat forwardly along the remaining stroke route, so that a small amount of liquid exits from the ampoule 4 through the needle 7. After the shoulder 56 has abutted against the supporting member 30' and thus the driving sleeve 10 can no longer be driven forwards, the head 11, upon being further depressed, moves against the bias of the spring 43 forwardly (downwardly) with respect to the driving sleeve 10, the extension 41 detaching itself from the ribs 40 and abutting, after an additional displacement z, against the shoulder 49. (As indicated in FIG. 9, the head 11 thus first moves, with respect to the shoulder 49—with the driving sleeve 10 and the threaded rod 12—by the stroke h, and subsequently—with the driving sleeve 10 and threaded rod 12 being stationary—still further by the additional stroke z.)

The elasticity constant of the spring 43 is chosen to be, on the one hand, adequately large as compared with that of the spring 26 in order to ensure that the extension 41 of the head 11 remains reliably retained on the ribs 40 until the driving sleeve 10, moved against the bias of the spring 26 and the friction of the plunger 5 in the ampoule 4, abuts against the supporting member 30' with its shoulder 56. On the other hand, the elasticity constant of the spring 43 is chosen to be at just such a value that the patient will hardly notice the abutting of the shoulder 56 against the supporting member 30', i.e. the pressure force required from the patient for overcoming the force of the spring 26 and the friction of the plunger 5 in the ampoule 4 is only unnoticeably smaller than the pressure force needed for moving the head 11 along the driving sleeve portion 10' against the force of the spring 43. Therefore, the patient will not recognize that the injection step is finished at the end of stroke h, and the additional stroke z is not necessary for the injection. The purpose of this additional stroke z resides in ensuring that the shoulder 56 of the driving sleeve 10 is reliably in contact with the supporting member 30' for a certain period of time, namely for the time period required for the additional stroke z. This prevents the patient from releasing the head 11 immediately after abutting of the shoulder 56 against the supporting member 30' so that the disk 17 at the end of the advance stroke h is immediately detached again from the plunger 5, and there is the danger that the plunger 5 does not remain in the advanced position but rather springs back somewhat.

After the extension 41 has abutted against the shoulder 49, and thus the head 11 cannot be advanced any further, the patient releases the head 11 whereupon the springs 26 and 43 move the driving sleeve 10, together with the threaded rod 12 carrying the disk 17, and the head 11 back into the position illustrated in FIGS. 8/9. (The driving sleeve 10 and the threaded rod 12 during this step move by the stroke h, the head 11 moves by the stroke h+z in the rearward direction with respect to the housing 1/2.)

For injecting a desired quantity of liquid, the patient turns the head 11 respectively (prior to inserting the needle 7) in the clockwise direction by a number of quarter turns corresponding to the desired number of liquid units; during this process, the patient has to overcome a stop position (of the stop mechanism 38/50) for each quarter turn (rotation by 90°), i.e. the amount of liquid can be dimensioned in accordance with the number of stop positions to be overcome. During rotation of the head 11 and thus also of the driving sleeve 10 nonrotationally (guide ribs 40) connected with the head, the threaded rod 12 entrained by the driving sleeve portion 10''' is threaded forwardly through the female thread 22 of the gear element 20, the spacing between the disk 17 and the plunger 5 being reduced without the disk touching the plunger. A rotation in the counterclockwise direction, by which the threaded rod 12 would be threaded backwards in the female thread 22, is prevented by the locking mechanism 51.

After the desired amount of liquid has been preselected by an appropriate turning of the head 11, the needle 7 is inserted and the head is pressed in the forward (downward) direction up to the stop (abutment of the extension 41 on the shoulder 49). During this step, as described above, the driving sleeve 10 is first urged against the force of the spring 26 forwards by the advance stroke h until the sleeve abuts against the supporting member 30', and then the head 11 is moved by the additional stroke z against the bias of the spring 43 with respect to the driving sleeve 10. During the feed stroke h, the disk 17 abuts against the plunger 5 and pushes same forwards by exactly the same amount that the threaded rod 12 has been turned in the forward direction by the previous rotation of the head in the female thread 22 of the gear element 20. The additional stroke z ensures here, as explained above, that the driving sleeve 10 with the threaded rod 12 remains for a certain amount of time at the end of the feed stroke h, and the plunger 5 is held, during this time, in the correct end position by the disk 17 so that it will no longer recede after the pressure relief.

When the ampoule 4 has been almost emptied, after repeated usage of the device, the flange 45 of the threaded rod 12 approaches the part 10''' of the driving sleeve. Then, finally, the case is encountered that the patient wants to inject a certain number of liquid units, but the head 11 can no longer be rotated by a corresponding number of quarter turns because the flange 45 abuts against the part 10''' during the revolutions. This conveys the knowledge to the patient that only an amount of liquid corresponding to the already executed number of quarter turns can be injected, rather than the entire quantity of liquid desired.

The length of the threaded rod and, respectively, the position of the flange 45 are dimensioned so that the plunger 5 during the advance stroke h of the threaded rod 12, in contact with its flange 45 at the member 10''' of the driving sleeve, can still be reliably advanced without abutting against the forward constriction of the ampoule 4. The patient thus has the assurance that the number of liquid units selected by turning the head 11 until abutting of the flange 45 against member 10''' can be reliably injected. And if the patient wishes to inject a specific number of liquid units, but the head can no longer be turned by the corresponding number of quarter turns, the patient has an indication that a new ampoule or a new injection device must be used to avoid dual injection (first the remainder from the old ampoule and then the still remaining difference from the new ampoule).

The injection device can be designed as a disposable unit, or the ampoule 4 can be exchanged. If the ampoule 4 is exchangeable then the threaded rod 12 must be threaded backwards by turning the head 11 in the counterclockwise direction through the female thread 22 until the disk 17 abuts against the front edge of the gear member part 21. For this purpose, the sawtooth profile surface of the collar 25' constituting the locking mechanism 51 must be detached from that of the shoulder 49. This can be achieved, as described in connection with FIGS. 1-7, by providing that the supporting member 30' is held in the housing 1/2 by the ampoule 4 so that it drops downwards upon removal of the ampoule whereby the spring 26 is relieved and the locking mechanism 51 as well as the stop mechanism 38, 50 are released. If the supporting member 30' is firmly anchored in the housing 1/2, the head 11 can be urged forwardly (downwardly) to a certain extent so that the sawtooth profile of the driving cellar 25' is detached from the sawtooth profile of the shoulder 49. However, in this case, the head must be maintained constantly in the depressed condition during the backward turning in the counterclockwise direction, and the locking resistance of the stop mechanism 38, 50 must be overcome upon each quarter turn.

I claim:

1. A dispenser device for dispensing selectable amounts of liquid from an elongated cylindrical container (4) having a plunger (5) slidable forward therein from one end thereof for forcing liquid out of the container through an outlet in the opposite end of the container, comprising a drive mechanism (3) having an elongated rod member (12, 17), and a carrier element (20), and displacing means (10, 11, 26), said carrier element (20) being displaceable forth and back in the advancing direction of the plunger (5), said rod member (12, 17) connected to and carried by said carrier element (20) in such a way that it can be axially advanced with respect to the carrier element (20) in the advancing direction of the plunger (5) and is positively carried by the carrier element (20) in the forward as well as in the backward direction, said displacing means (10, 11, 26) being connected on the one hand to advance the rod member (12, 17) with respect to the carrier element (20) and on the other hand to advance and retract the carrier element (20) together with the rod member (12, 17) carried thereby with respect to the container (4), the rod member (12, 17) being adapted to abut and force the plunger (5) forward during activation of said displacing means (10, 11, 26) for advancing the carrier element (20) together with the rod member (12, 17) with respect to the container (4), housing means (1, 2), said cylindrical container (4) and said drive mechanism (3) connected in said housing means axially to each other, said displacing means (10, 11, 26) including a manually engageable element (11) extending from said housing means (1, 2), said rod member (12, 17) positioned to push the plunger (5) of the cylindrical container (4) forward and to move away from said plunger (5) leaving the latter in the forward pushed position, said displacing means (10, 11) connected for axially displacing said carrier element (20) by a constant stroke (h) forth and back in the advancing direction of the plunger (5) from a rearward rest position in said housing means (FIG. 2; FIG. 9) to a forward position (FIG. 3) axially toward the plunger (5), and back again into the rest position (FIG. 2; FIG. 9), said rod member (12, 17) on the one hand being axially advanceable by means of said displacing means (10, 11) with respect to said carrier element (20) in the advancing direction of the plunger (5) by any selected distance in correspondence with the plunger path, required for the desired quantity of liquid to be dispensed from said cylindrical container (4), and on the other hand said rod member (12, 17) being displaceable forth and back together with said carrier element (20) by said constant stroke (h) by said displacing means (10, 11), whereby said rod member (12, 17) located at a distance from the plunger (5) in the rest position (FIG. 2; FIG. 9) of the carrier element (20) can be axially moved, by means of said displacing means (10, 11), relative to the carrier element (20) remaining in the rest position (FIG. 2; FIG. 9), in the advancing direction by the selected axial distance without abutting against the plunger (5), and abuts during actuation and displacement (h) of the carrier element (20) from the rest position (FIG. 2; FIG. 9) into the forward position (FIG. 3) against the plunger (5) at the moment, when the carrier element (20) has been axially displaced by the difference between the constant stroke (h) and the selected distance, when the displacement of the carrier element (20) is continued up to the forward position (FIG. 3), and means (26) connected to move said carrier element (20) and rod member (12, 17) away from the plunger (5) by the constant stroke (h) leaving the plunger (5) in the forward pushed position, while displacing the carrier element (20) back from the forward position (FIG. 3) into the rest position (FIG. 2; FIG. 9).

2. Device according to claim 1, including a support element (30, 31, 30') in said housing positioned stationary relative to said one end of said container (4), a spring (26) having one end engaging said support element (30, 31, 30') and another end engaging said carrier element (20), said carrier element (20) being held by said spring (26) in the rest position and is displaceable into the forward position against the spring force.

3. Device according to claim 2, in which said displacing means comprises a drive sleeve (10), said manually engageable element comprising a manipulating head (11) connected on the drive sleeve at the end of the device facing away from the container (4), said rod member (12, 17) slidably received within the drive sleeve (10), the drive sleeve (10) coupled to said rod member (12, 17) and being rotatable by means of this head to rotate said rod member (12, 17) and thereby axially advance said rod member (12, 17) relative to said carrier element (20), and said drive sleeve (10) connected axially to said carrier element (20), said drive sleeve (10) axially moveable by axial movement of said head to move said rod member (12, 17) together with the carrier element (20) from the rest position into the forward position.

4. Device according to claim 3, in which said manipulating head (11) is mounted (40) nonrotationally but longitudinally displaceably on the drive sleeve (10), a second spring (43) connected between said head (11) and said drive sleeve (10), a part (40) of the drive sleeve (10) retaining said head (11) thereon against the force of said second spring (43) acting upon the head in opposition to the advancing direction; and that the elasticity constant of the second spring (43) is larger than that of the first said spring (26) so that, when the manipulating head (11) is depressed, the latter is first advanced from the rest position into the forward position against the force of the first spring (26) together with the drive sleeve (10), the carrier element (20) and the rod member (12, 17), and directly subsequently, while continuing the exertion of pressure on the manipulating head (11), the head is advanced with respect to the drive sleeve (10) against the force of the second spring (43), during which step the drive sleeve (10), the carrier element (20) and the rod member (12, 17) remain in the forward position.

5. Device according to claim 3, in which said manually drivable mechanism (3) includes an automatic locking mechanism (51) connected to release the rotational movement of the drive sleeve (10, 11) in the direction of rotation wherein the rod member (12, 17) can be operated in the advancing direction toward the container (4), and blocks such rotational movement in the opposite direction of rotation.

6. Device according to claim 5, including a projection (27, 47) formed on the carrier element (20), said spring (26) clamped between said support element (30, 31, 30') and said projection (27, 47), the drive sleeve (10, 25') and the carrier element (20, 47) having a pair of mating annular surfaces (25', 49) pressed into mutual contact by the force of said spring (26), said pair of annular surfaces (25', 49) having mating sawtooth-like peripheral projections (51) constituting the locking mechanism.

7. A device according to claim 5, in which said container (4) is an exchangeable container, said spring (26) biasing said locking mechanism (51), said support element (30, 31, 30') axially supported on the container (4), whereby upon removal of the container (4) from said housing means (1, 2) the biasing force of said spring (26) being relieved so it no longer exerts a biasing force on the locking mechanism (51) and the drive sleeve (10, 11) can be rotated in said opposite direction of rotation normally blocked by said locking mechanism (51).

8. A device according to claim 5, in which said container (4) is an exchangeable container, said support element (30, 31, 30') in said housing means (1, 2) supported on the container, said spring (26) biasing said locking mechanism (51), said support element (30, 31, 30') upon removal of the container (4) slides forward in said housing means to a position whereby said spring (26) no longer exerts a biasing force on said locking mechanism (51), whereby the drive sleeve (10, 11) can be rotated in said opposite direction of rotation normally blocked by said locking mechanism (51).

9. Device according to claim 2, in which said displacing means (10, 11) includes a drive sleeve (10), said carrier element (20) is pressed axially against the drive sleeve (10, 25) by the force of the spring (26), and a stop (37; 49) on the housing means for the drive sleeve (10, 25) determining the rest position of said carrier element (20).

10. Device according to claim 2, in which said displacing means (10, 11) comprises a rotatable drive sleeve (10, 11) and a stop mechanism (38) between said housing means and drive sleeve (10, 11), said stop mechanism operative to lock in place once or repeatedly during each full revolution of the drive sleeve (10, 11), said stop mechanism biased by said spring (26) whereby during manual rotation of the drive sleeve (10, 11) a noticeable stop resistance must in each case be overcome, and the amount of liquid to be respectively dispensed from said container can be determined in accordance with the number of stop positions to be overcome.

11. Device according to claim 9 or 10, in which the stop includes projections (38) and mating indentations (50) on the drive sleeve (10, 25; 10, 25') and on the carrier element (20, 23; 20, 47) placed into mutual contact by the pressure of the spring (26).

12. Device according to claim 10, in which said container (4) is an exchangeable container (4), the spring (26) biasing the stop mechanism (38, 50) is supported on the support element (30, 31, 30') abutting said one end of said container (4) or on the container, whereby upon removal of the container (4) from said housing means (1, 2) the spring (26) no longer exerts any biasing force on the stop mechanism, so that the drive sleeve (10, 11)

after removal of the container (4) can be rotated without overcoming a stop resistance.

13. A device according to claim 10, in which said container (4) is an exchangeable container, said support element (30, 31, 30') in said housing means (1, 2) supported on the container, said spring (26) biasing the stop mechanism (38, 50) supported on said support element (30), said support element (30) upon removal of the container (4) slides forward in the housing means to a position whereby said spring (26) no longer exerts any biasing force on said stop mechanism (38, 50), or exerts only a minor biasing force thereon, whereby the drive sleeve (10, 11) can be rotated without overcoming a stop resistance.

14. Device according to claim 1, in which said displacing means (10, 11) comprising a driving sleeve (10), and said manually engageable element (11) connected on one end of said driving sleeve (10), said driving sleeve (10) having a forward portion (10''') and rotatable manually directly by means of said manually engageable element (11), and the rod member is constituted by a threaded rod (12) which is slidably received within said driving sleeve (10) and coupled thereto to be longitudinally displaceable by the driving sleeve (10) and nonrotationally at least in the forward portion (10''') of the sleeve; guide means (33, 34; 30') in said housing means, and said carrier element (20) having a thread portion (22) threadably engaging the threaded rod (12), and said carrier element (20) slidably engaging said guide means (33, 34; 30') thereby securing said carrier element against rotation.

15. Device according to claim 14, including a flange (45) at the end of said threaded rod (12) away from the plunger (5), said driving sleeve (10) having an inner wall, the inner wall of the driving sleeve (10) is designed only in the forward portion (10''') for the nonrotational mounting of the threaded rod (12) therein and is constructed, in the remaining part, with spacing to the flange (45); and that the length of the threaded rod (12) and, respectively, the position of the flange (45) on the threaded rod (12) are dimensioned with respect to the length of the container (4) in such a way that the plunger (5) of the container can still be reliably advanced during the advance stroke (h) of the threaded rod (12), which latter has abutted with its flange (45) against the forward portion (10''') of the driving sleeve (10), without the plunger abutting against the opposite end of the container (4).

16. Device according to claim 14, characterized in that the carrier element (20) having a forward portion (21) which is at the front thereof in the direction toward said container (4) which includes the thread portion (22) engaging the threaded rod (12), and the carrier element (20) having a rearward part (23) that includes a threadless bore wherein the driving sleeve (10) is rotatably supported; and that the driving sleeve (10) and the carrier element (20) are supported against each other (25, 23; 25', 47).

* * * * *